(12) United States Patent
Preston et al.

(10) Patent No.: US 8,336,551 B1
(45) Date of Patent: Dec. 25, 2012

(54) CANNULA SUPPORT DEVICE

(76) Inventors: Mary A. Preston, Minot, ND (US);
Cynthia M. Muchacho, Lake Lillian, MN (US)

(*) Notice: Subject to any disclaimer, the term of this patent is extended or adjusted under 35 U.S.C. 154(b) by 0 days.

(21) Appl. No.: 13/017,077

(22) Filed: Jan. 31, 2011

(51) Int. Cl.
*A61M 15/08* (2006.01)
*A62B 7/00* (2006.01)

(52) U.S. Cl. .................................. 128/207.18

(58) Field of Classification Search ............ 128/206.11, 128/206.21, 206.27, 207.11, 207.13, 207.18, 128/DIG. 26; 24/3.1, 3.4, 3.12; 604/174
See application file for complete search history.

(56) References Cited

U.S. PATENT DOCUMENTS

| | | | |
|---|---|---|---|
| 4,742,824 A | 5/1988 | Payton et al. | |
| 4,836,200 A | 6/1989 | Clark | |
| 4,915,104 A | 4/1990 | Marcy | |
| 5,105,807 A * | 4/1992 | Kahn et al. | 128/207.18 |
| 5,308,337 A | 5/1994 | Bingisser | |
| 5,704,916 A | 1/1998 | Byrd | |
| 6,804,866 B2 | 10/2004 | Lemke et al. | |
| 6,986,353 B2 | 1/2006 | Wright | |
| 7,156,097 B2 | 1/2007 | Cardoso | |
| 2004/0139973 A1* | 7/2004 | Wright | 128/207.18 |
| 2008/0276941 A1* | 11/2008 | Doty et al. | 128/205.28 |
| 2011/0067704 A1* | 3/2011 | Kooij et al. | 128/207.18 |

* cited by examiner

*Primary Examiner* — Kristen Matter
(74) *Attorney, Agent, or Firm* — Montgomery Patent & Design, LLC; Robert C. Montgomery; Joseph Yaksich

(57) ABSTRACT

A cannula support device holds an oxygen cannula in place on a user's face and includes a pair of collars utilized on each side of a user's face, thereby providing a fit to existing cannula tubing. Each set of collars is interconnected with thread that is laced back and forth forming a harness structure. The device supports existing oxygen tubing in place while alleviating excessive pressure which is normally associated with oxygen cannula.

20 Claims, 3 Drawing Sheets

CANNULA SUPPORT DEVICE

RELATED APPLICATIONS

The present invention was first described in a notarized Official Record of Invention on Apr. 7, 2010, that is on file at the offices of Montgomery Patent and Design, LLC, the entire disclosures of which are incorporated herein by reference.

FIELD OF THE INVENTION

The present invention relates generally to oxygen delivery nasal cannula, and in particular, to support device for retaining a nasal cannula in place upon a wearer's face.

BACKGROUND OF THE INVENTION

It is an all too familiar scene in a hospital or extended care facility where a patient that requires oxygen or other similar gases is seen constantly fidgeting with the oxygen tube worn across their face or nasal cannula inserted in their nose. More often than not, the cause of their discomfort originates from the cannula tubing that is routed behind their ears. This tubing is relatively hard in nature and generates pressure on the ear and cheek area, especially after prolonged periods of use.

Various attempts have been made to overcome these problems and alleviate these discomforts. Some care providers take foam padding and tape it to the ear pieces to help alleviate this discomfort. Various other types of oxygen tube support devices have also been provided. Examples of such attempts can be seen by reference in several U.S. patents. U.S. Pat. No. 4,742,824, issued to Payton et al., describes an oxygen tube support patch having an adhesive face patch for support of the oxygen tube. U.S. Pat. No. 4,836,200, issued to Clark, discloses an oxygen tube support strap including a head strap having loops to hold the oxygen tubes. U.S. Pat. No. 5,704,916, issued to Byrd, discloses an oxygen tube support apparatus and associated method including a strap worn across the top of the head of a patient having two (2) opposite ends with adhesive sides for retaining the branches of the cannula between the adhesive ends. Other attempts include complex nasal oxygen delivery tubes, as seen in U.S. Pat. No. 4,915,104, issued to Marcy and U.S. Pat. No. 6,986,353, issued to Wright.

While these devices may achieve their particularly stated objectives, they each suffer from one (1) or more disadvantage or deficiency related to design or utilization. Particularly, the foam padding is known to turn and rollover thus causing additional discomfort and distraction to the patient. Strap devices worn over the head tend to shift when worn, especially when the patient is sleeping, which can dislodge the nostril prongs and add to discomfort and lack of oxygen being supplied to the patient. Complicated oxygen tubes can add additional time to set up and can be even more uncomfortable and obtrusive to the patient.

SUMMARY OF THE INVENTION

The inventor has therefore recognized the aforementioned inherent problems and lack in the art and observed that there is a need for a means by which patients utilizing a nasal cannula can be afforded comfort around their ear and cheek area without the disadvantages as mentioned above. It is an object of the present disclosure to solve these problems.

The inventor recognized these problems and has addressed this need by developing a cannula support device which provides patients on oxygen for a long term increased comfort in a manner which is quick, easy, and effective. The inventor has thus realized the advantages and benefits of providing a pair of split collars, where each of the split collars includes a hollow cylindrical body having a longitudinal slit to bifurcate the cylindrical body and a plurality of apertures disposes longitudinally across the cylindrical body adjacent to the slit. At least one (1) thread member is interwoven within the plurality of apertures and between the pair of split collars for joining the split collars together. The slit allows for attachment to an oxygen delivery tube of the nasal cannula inserted therein, such that the split collar encompasses the oxygen delivery tube. The pair of split collars is mounted between an upper portion and a lower portion of the oxygen delivery tube when placed around an ear of the wearer.

Furthermore, the described features and advantages of the disclosure may be combined in various manners and embodiments as one skilled in the relevant art will recognize. The disclosure can be practiced without one (1) or more of the features and advantages described in a particular embodiment.

Further advantages of the present disclosure will become apparent from a consideration of the drawings and ensuing description.

BRIEF DESCRIPTION OF THE DRAWINGS

The advantages and features of the present disclosure will become better understood with reference to the following more detailed description and claims taken in conjunction with the accompanying drawings, in which like elements are identified with like symbols, and in which:

DESCRIPTIVE KEY

Figure 1:
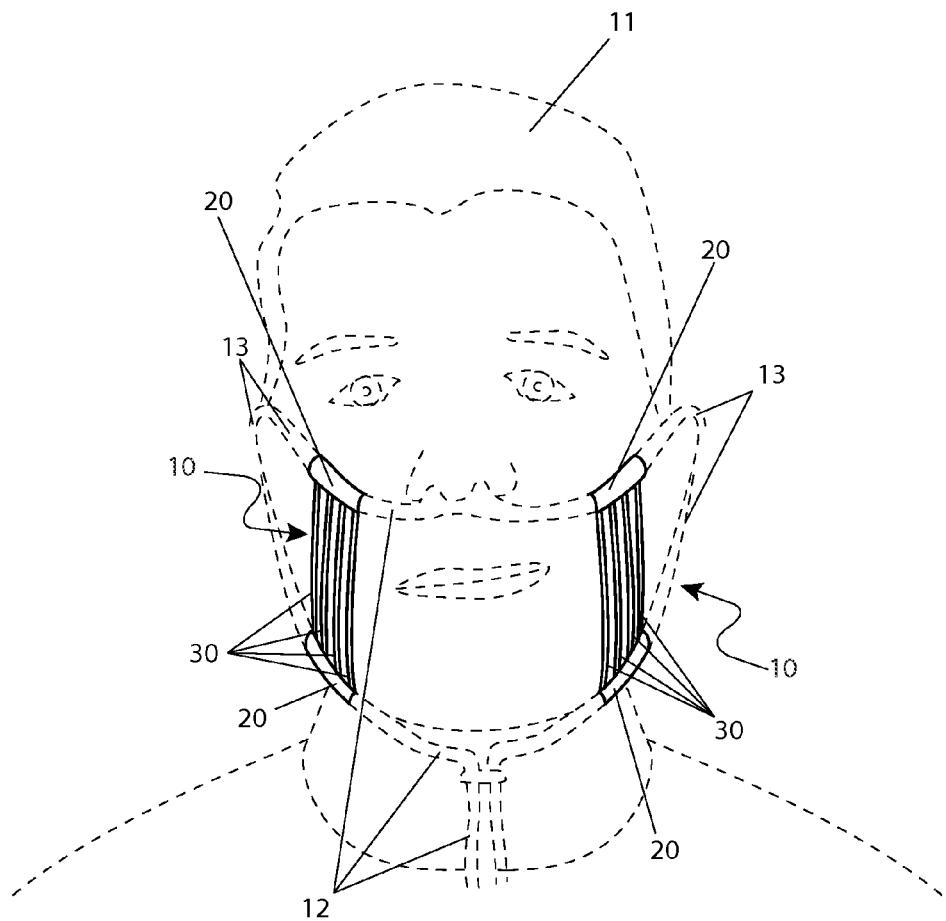
FIG. 1 is an environmental view of a cannula support device 10, according to a preferred embodiment.

10 cannula support device
11 cheek region
12 nasal oxygen cannula
13 ear anchoring loop
20 split collar
21 slit
22 aperture
30 thread
31 knot

DETAILED DESCRIPTION OF THE PREFERRED EMBODIMENT

The best mode for carrying out the disclosure is presented in terms of a preferred embodiment, herein depicted within FIGS. 1 through 4. However, the disclosure is not limited to a single described embodiment and a person skilled in the art will appreciate that many other embodiments are possible without deviating from the basic concept of the disclosure and that any such work around will also fall under its scope. It is envisioned that other styles and configurations can be easily incorporated into the teachings of the present disclosure, and only one particular configuration may be shown and described for purposes of clarity and disclosure and not by way of limitation of scope.

The terms "a" and "an" herein do not denote a limitation of quantity, but rather denote the presence of at least one of the referenced items.

The present invention describes a cannula support device (herein described as a "device") 10, which holds nasal oxygen cannula 12 in place on user's face. The device 10 allows the nasal oxygen cannula 12 to remain in place while alleviating excessive pressure upon the cheeks and ears of the user which is normally associated with the placement of the nasal oxygen cannula 12. It is particularly useful when used as a pair of devices 10.

Referring now to FIG. 1, an environmental view of the device 10 is disclosed. The device 10 includes a pair of split collars 20 and a length of thread 30 which provides a securing feature to retain the nasal oxygen cannula 12 in an ear anchoring loop 13 which positions the nasal oxygen cannula 12 behind the user's ears and under the user's chin. The device 10 is preferably utilized in pairs with one (1) device 10 on each side of the user's face. Each device 10 is positioned upon each cheek region 11 of the user's face and attached to an upper and lower portion of the nasal oxygen cannula 12. The device 10 preferably includes a range of sizes to accommodate various sized nasal oxygen cannula 12 and various sized users.

Figure 2:
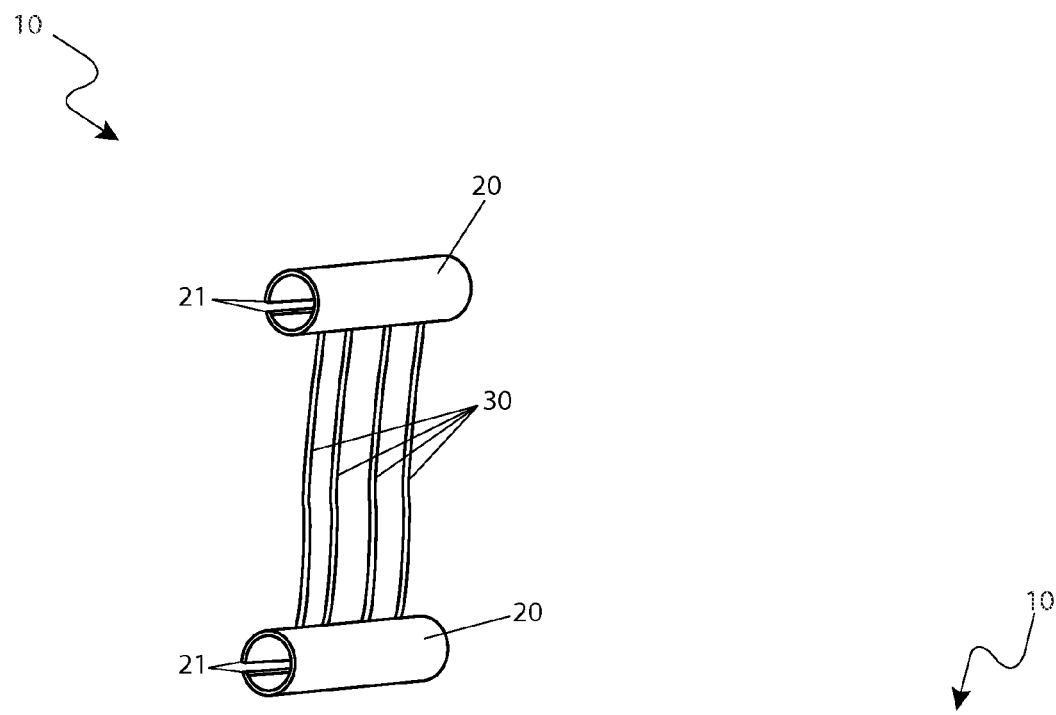
FIG. 2 is a perspective view of the cannula support device 10, according to the preferred embodiment.
Figure 3:
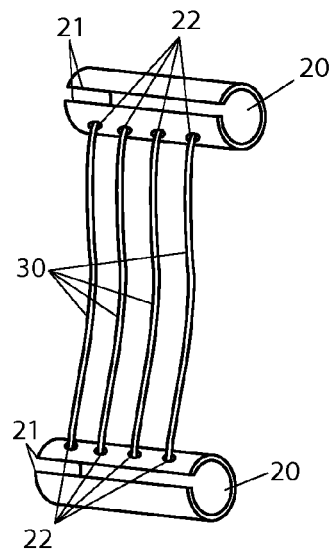
FIG. 3 is an opposing perspective view of the cannula support device 10, according to the preferred embodiment; and, FIG. 4 is a perspective view of the cannula support device 10 depicted in an opened state, according to the preferred embodiment.

Referring now to FIG. 2, a perspective view of the device 10 and FIG. 3, an opposing perspective view of the device 10 are disclosed. FIGS. 2 and 3 depict a single device 10; it is understood that a pair of devices 10 should be utilized during application purposes. Each split collar 20 provides for the attachment to the nasal oxygen cannula 12 and a tension to the opposing split collar 20, thereby relieving pressure behind the user's ears and a region below the user's eyes. The split collars 20 include a cylindrical shape which preferably measures approximately one (1) inch in length and further include a diameter slightly larger than a diameter of the tubing utilized on the nasal oxygen cannula 12. Each split collar 20 includes a slit 21 and a plurality of apertures 22. The split collars 20 are preferably fabricated from a semi-rigid transparent material such as, but not limited to: plastic, silicone, or the like so as to provide strength and discreetness when in use. The split collars 20 should also include excellent memory characteristic so as to retain its original cylindrical shape after being deformed.

Each slit 21 allows for attachment to the inserted nasal oxygen cannula 12. The slit 21 extends longitudinally across the split collars 20 and enables the split collars 20 to encompass and wrap around an intermediate location of the tubular portion of the nasal oxygen cannula 12. The slit 21 also retains the length and form of the ear anchoring loops 13 by allowing the user to position the split collars 20 in a location for optimal comfort and protection as desired.

The apertures 22 are oriented in a row along opposing perimeter longitudinal edges of each split collar 20 to connection the pair of split collars 20 by a length of thread 30. The apertures 22 accept the thread 30 to provide a specific gap between each split collar 20 which preferably measures one-and-a-half (1½) inches in length, yet other dimensions may be utilized without limiting the scope of the device 10.

Figure 4:
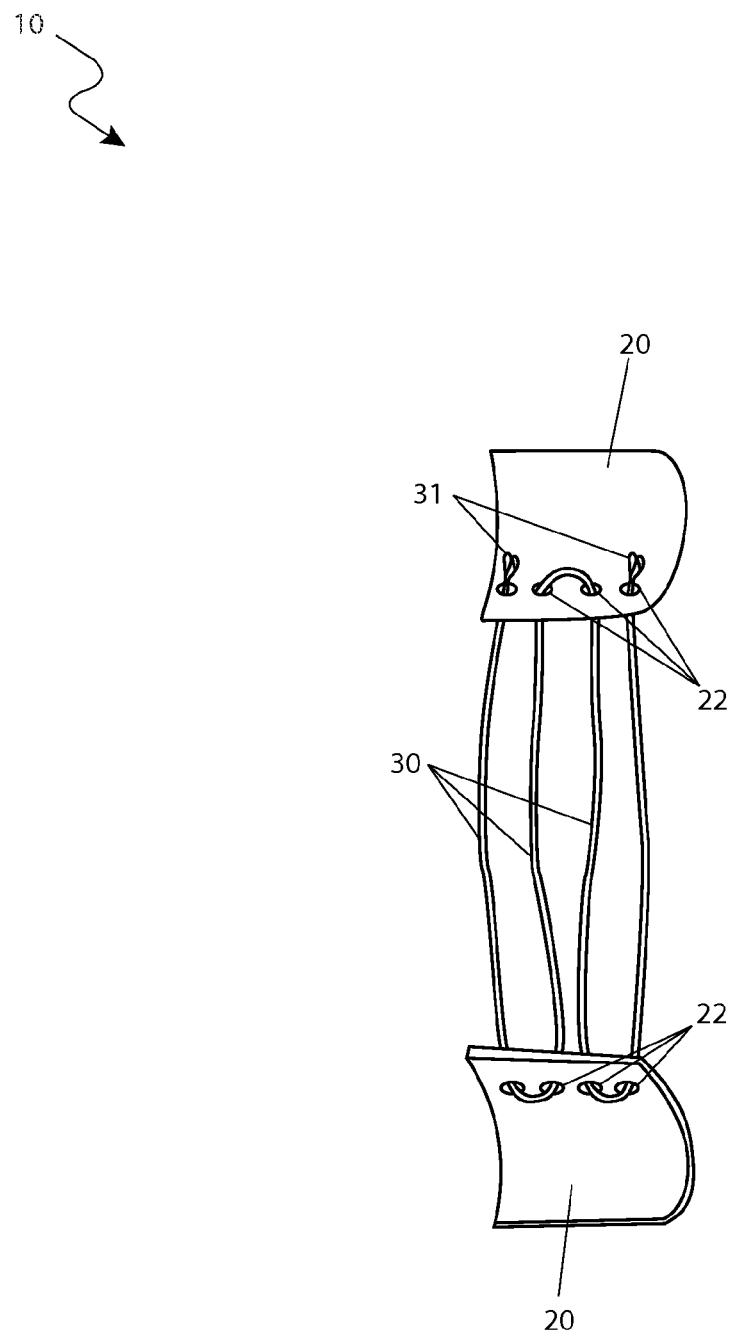

Referring now to FIG. 4, a perspective view of the device 10 depicted with the split collars 20 in an open state, is disclosed. FIG. 4 depicts each split collar 20 slightly deformed to illustrate the lacing and securing of the thread 30; however it is understood that the material utilized for construction of the split collars 20 would enable flexibility. The thread 30 is fabricated from a transparent monofilament line to provide discreetness and strength. The thread 30 is preferably arranged in pairs of strands so as to provide additional strength while being exposed to the rigors of daily wear. The thread 30 is interwoven between each aperture 22 and secured at each end by a knot 31, crimp, other integral attachment including plastic or sonic welding.

It is envisioned that other styles and configurations can be easily incorporated into the teachings of the present disclosure and only one particular configuration has been shown and described for purposes of clarity and disclosure and not by way of limitation of scope.

The preferred embodiment can be utilized by the common user in a simple and effortless manner with little or no training. After initial purchase or acquisition of the device 10, it would be installed as indicated in FIG. 1.

The method of utilizing the device 10 may be achieved by performing the following steps: acquiring the device 10; with an existing nasal oxygen cannula 12 upon the user attach each split collar 20 onto the upper and lower the nasal oxygen cannula 12 tubing to a desired location; and, providing the user on oxygen with increased comfort in a manner which is quick, easy, and effective.

The method of restringing the device 10 may be achieved by performing the following steps: threading the thread 30 through each aperture 22 and creating a knot 31 at each end portion.

The foregoing descriptions of specific embodiments have been presented for purposes of illustration and description. They are not intended to be exhaustive or to limit to the precise forms disclosed and many modifications and variations are possible in light of the above teachings. The embodiments were chosen and described in order to best explain principles and practical application to enable others skilled in the art to best utilize the various embodiments with various modifications as are suited to the particular use contemplated.

What is claimed is:

1. A support device for retaining a nasal cannula in place upon a wearer's face, said device comprising:
    a pair of split collars, each of said split collars further comprises a hollow cylindrical body having a longitudinal slit bifurcating said cylindrical body and a plurality of apertures disposed longitudinally across said cylindrical body adjacent to said slit; and,
    at least one thread member interwoven within said plurality of apertures and between said pair of split collars for joining said split collars together;
    wherein said slits are adapted for attachment to an oxygen delivery tube of said nasal cannula inserted therein, such that said split collars encompass said oxygen delivery tube; and,
    wherein said pair of split collars is mounted between an upper portion and a lower portion of said oxygen delivery tube when placed around an ear of said wearer.

2. The device of claim 1, wherein each of said split collars is approximately one inch long.

3. The device of claim 2, wherein each of said split collars further comprises an internal diameter suitable to receive said oxygen delivery tube.

4. The device of claim 3, wherein each of said split collars is formed from a semi-rigid, transparent material.

5. The device of claim 3, wherein each of said split collars is formed of a shape-memory polymer.

6. The device of claim 1, wherein a distance between said pair of joined split collars is approximately one and one half inches.

7. The device of claim 1, wherein said at least one thread member further comprises a transparent monofilament line.

8. The device of claim 7, wherein said at least one thread member is secured at each end within a prescribed aperture by a knot.

9. The device of claim 7, wherein said at least one thread member is secured at each end within a prescribed aperture by a crimp.

10. The device of claim 7, wherein said at least one thread member is integrally affixed at each end within a prescribed aperture.

11. The device of claim 1, whereby the placement of said pair of split collars upon said oxygen delivery tube is adjustable.

12. A support device for retaining a nasal cannula in place upon a wearer's face, said device comprising:
   a generally tubular first collar having a longitudinal first slit bifurcating said first body and at least one first aperture adjacent to said first slit;
   a generally tubular second collar having a longitudinal second slit bifurcating said second body and at least one second aperture adjacent to said second slit; and,
   at least one thread member attached between said at least one first aperture and said at least one second aperture for joining said first body and said second body together;
   wherein said slits are adapted for insertion of an oxygen delivery tube of said nasal cannula, such that said first and second collars encompass said oxygen delivery tube; and,
   wherein said first collar and said second collar are mounted between an upper portion and a lower portion of said oxygen delivery tube when placed around an ear of said wearer.

13. The device of claim 12, wherein said first collar further comprises a plurality of longitudinally disposed first apertures and said second collar further comprises a plurality of longitudinally disposed second apertures; and,
   wherein said device further comprises a plurality of thread members attached between said plurality of first apertures and said plurality of second apertures.

14. The device of claim 13, wherein each of said collars is approximately one inch long and further comprises an internal diameter suitable to receive said oxygen delivery tube.

15. The device of claim 14, wherein a distance between said first collar and said second collar is approximately one and one half inches.

16. The device of claim 15, wherein said plurality of thread members further comprises a transparent monofilament line.

17. The device of claim 16, wherein each of said collars are formed from a semi-rigid, transparent material.

18. The device of claim 17, wherein said plurality of thread members is secured at each end within a prescribed aperture by a knot.

19. The device of claim 18, whereby the placement of said pair of split collars upon said oxygen delivery tube is adjustable.

20. A method of retaining a nasal cannula in place upon a wearer's face, said method comprising the steps of:
   providing said nasal cannula comprising at least an oxygen delivery tube which fits behind the ears of said wearer and a set of prongs which are placed in the nostrils of said wearer;
   providing at least two support devices each comprising a pair of split collars, each of said split collars further comprising a hollow cylindrical body having a longitudinal slit bifurcating said cylindrical body and a plurality of apertures disposed longitudinally across said cylindrical body adjacent to said slit; and, at least one thread member interwoven within said plurality of apertures and between said pair of split collars for joining said split collars together;
   positioning said nasal cannula upon said wearer, around said ears and across a face;
   inserting an upper portion of said oxygen delivery tube of said nasal cannula within said slit of one of said pair of split collars and inserting a lower portion of said oxygen delivery tube of said nasal cannula within said slit of an opposing one of said pair of split collars on one side of said wearer's face;
   inserting an upper portion of said oxygen delivery tube of said nasal cannula within said slit of one of said pair of split collars and inserting a lower portion of said oxygen delivery tube of said nasal cannula within said slit of an opposing one of said pair of split collars on an opposite side of said wearer's face; and,
   adjusting a location of each of said split collars for comfort.

\* \* \* \* \*